US00PP29593P3

(12) United States Plant Patent
Suphachadiwong

(10) Patent No.: US PP29,593 P3
(45) Date of Patent: Aug. 14, 2018

(54) ***VANDA* PLANT NAMED 'SPCDW1608'**

(50) Latin Name: ***Vanda* spp. Jones ex R. Br.**
Varietal Denomination: SPCDW1608

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,167

(22) Filed: Sep. 27, 2017

(65) Prior Publication Data

US 2018/0092275 P1 Mar. 29, 2018

(30) Foreign Application Priority Data

Sep. 27, 2016 (QZ) ..... PBR 2016/2333

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Annette H Para
(74) *Attorney, Agent, or Firm* — Samuel R. McCoy, Jr.

(57) ABSTRACT

A new and distinct variety of *Vanda* plant named 'SPCDW1608' which is characterized by numerous large flowers borne on a tall inflorescence, flowers with light pink petals and sepals which are heavily dotted and blotched with dark red-purple, a labellum with a dark red-purple central lobe and light pink lateral lobes which are radially striped purple, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1608'.

CROSS REFERENCE TO RELATED APPLICATIONS

This application claims priority to the Community Plant Variety Rights application number 2016/2333, filed Sep. 27, 2016, which is herein incorporated by reference.

BACKGROUND OF THE INVENTION

Parentage: The *Vanda* variety 'SPCDW1608' is the result of a planned breeding program. The new variety originated as a seedling from the crossing of *Vanda* 'M38BP' (not patented), the seed parent, with *Vanda* 'M409' (not patented), the pollen parent. Both parents were developed by, and are owned by, the inventor and were never commercially released. The crossing was made by the inventor in his research greenhouse in Bangphra, Thailand in December of 2004.

The new variety was first selected in May of 2008, in a research greenhouse in Bangphra, Thailand belonging to the inventor. After identifying the new variety as a potentially interesting selection, the inventor continued confidential testing and propagation of 'SPCDW1608', assessing stability of the unique characteristics of this variety.

Asexual Reproduction: Asexual reproduction of the new cultivar 'SPCDW1608', by way of mericloning, was first initiated in August of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1608' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1608'. These characteristics in combination distinguish 'SPCDW1608' as a new and distinct *Vanda* cultivar:

1. *Vanda* 'SPCDW1608' exhibits numerous large flowers borne on a tall inflorescence; and
2. *Vanda* 'SPCDW1608' exhibits flowers with light pink petals and a light pink dorsal sepal, all of which are heavily dotted with dark red-purple; and
3. *Vanda* 'SPCDW1608' exhibits light pink lateral sepals which are all densely dotted and blotched with dark red-purple; and
4. *Vanda* 'SPCDW1608' exhibits a labellum with a dark red-purple central lobe, and light pink lateral lobes which are radially striped purple.

BOTANICAL DESCRIPTION OF THE PLANT

Figure 1:
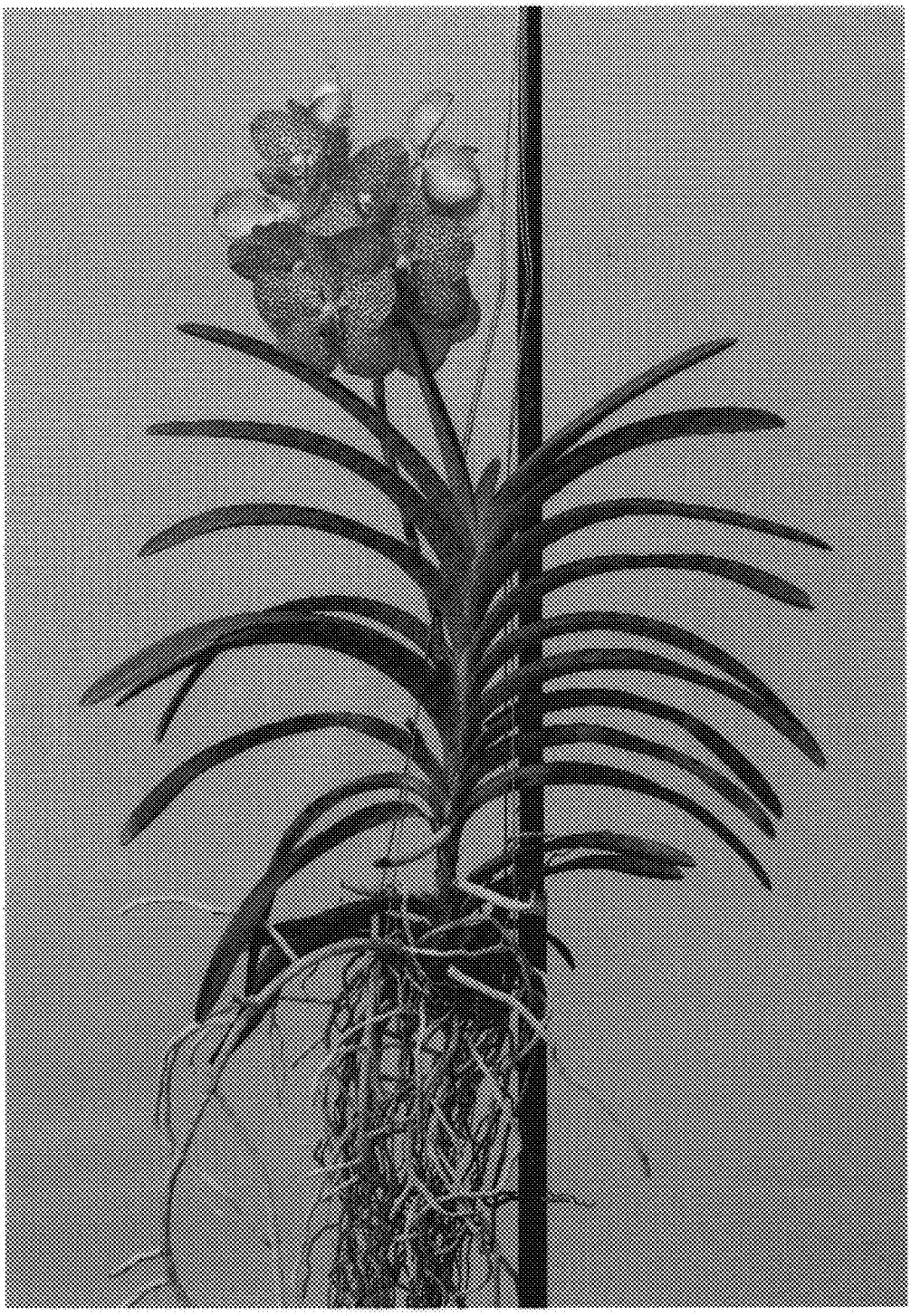
FIG. 1 illustrates, as nearly true as it is reasonably possible to make the same in color photographs of this type, an exemplary plant of 'SPCDW1608' grown in a commercial greenhouse in Honselersdijk, the Netherlands. This plant is approximately 6 years old from the time of mericloning, shown planted in an 8 by 8 cm container.
Figure 2:
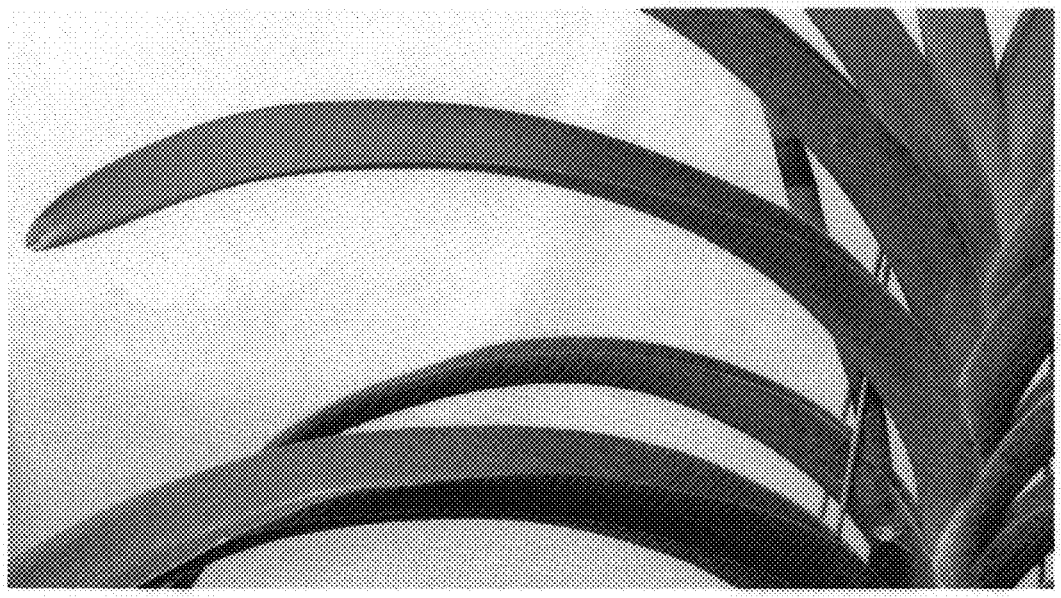
FIG. 2 illustrates, as nearly true as it is reasonably possible to make the same in color photographs of this type, the typical foliage of 'SPCDW1608'.
Figure 3:
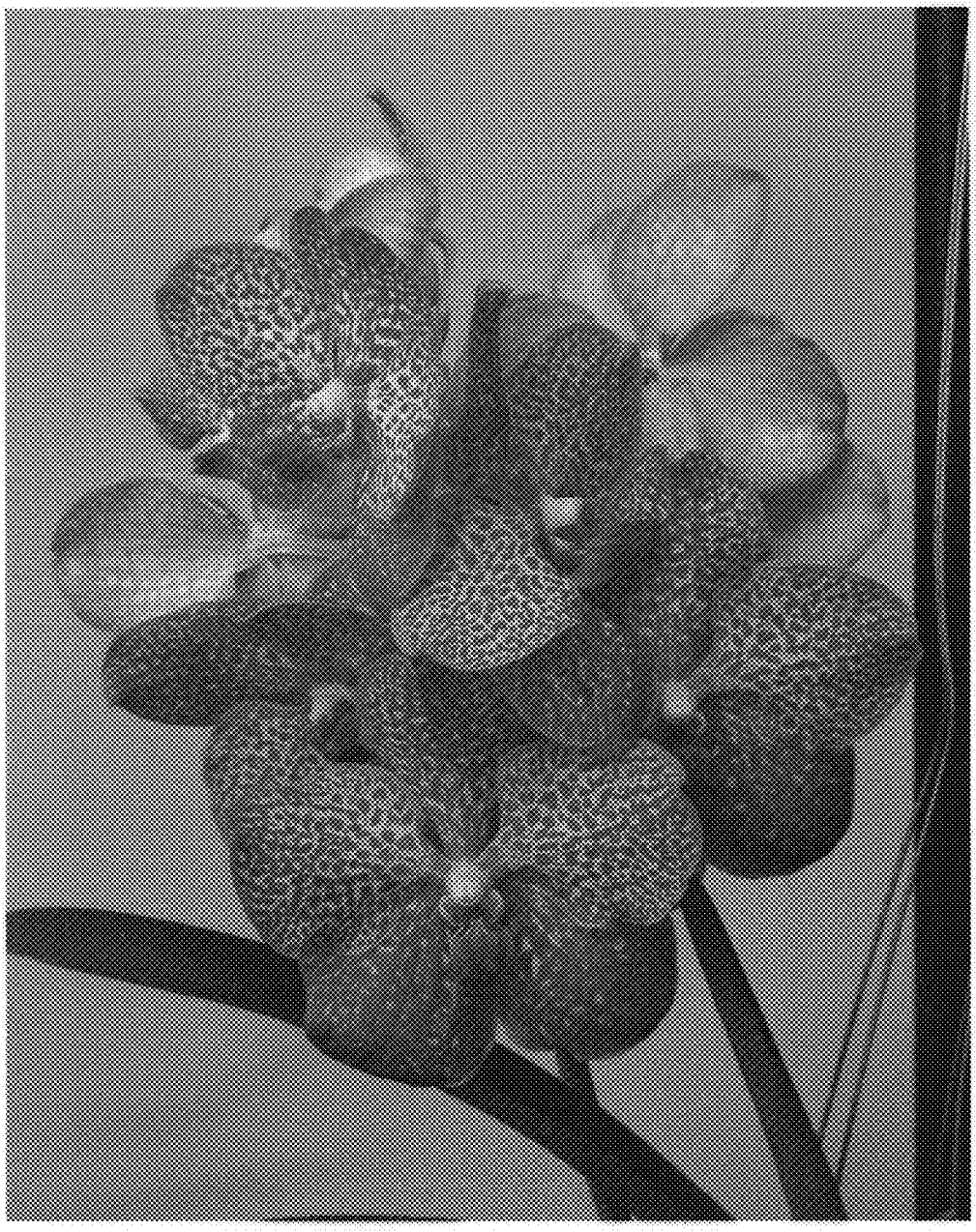
FIG. 3 illustrates, as nearly true as it is reasonably possible to make the same in color photographs of this type, the typical inflorescence of 'SPCDW1608'.
Figure 4:
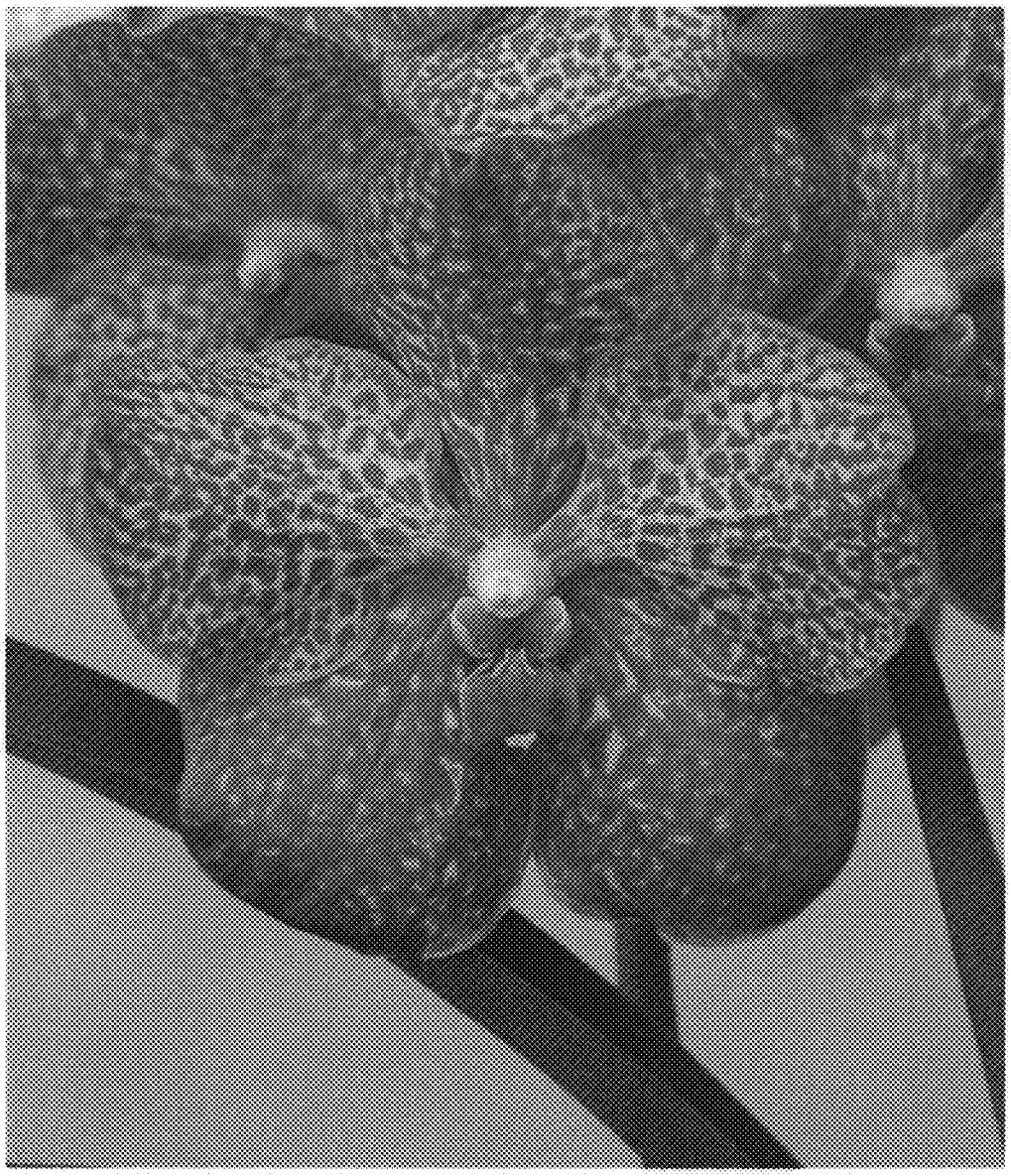
FIG. 4 illustrates, as nearly true as it is reasonably possible to make the same in color photographs of this type, the typical flower of 'SPCDW1608'.

The following observations and measurements made in September of 2017 describe averages from a sample set of six specimens of six year-old 'SPCDW1608' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1608' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1608' and comparisons with the parents and most similar commercial variety of *Vanda* are provided below.

Plant description:

*Growth habit*.—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane*.—46.6 cm.

*Average height from base (plant grown in hanging basket, so no soil line present) to top of floral plane*.—59.9 cm.

*Plant spread*.—Average of 42.8 cm.

*Appropriate container size*.—8 cm by 8 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately dense rooting; with aerial roots only.

*Dimensions, mature roots*.—67.1 cm long with a diameter of 0.5 cm, on average.

*Texture*.—Very fleshy; non-fibrous.

*Color*.—Greyed-green, nearest to a combination of RHS 192C and 192D; root apex is yellow-green, RHS 148A.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—27.5 cm.

*Diameter*.—1.0 cm.

*Internode length*.—1.1 cm.

*Luster*.—Matte.

*Aspect, main stem*.—Near vertical.

*Strength*.—Very strong.

*Color, juvenile*.—Yellow-green, nearest to a combination of RHS 145C and 145D.

*Color, mature*.—Yellow-green, nearest to RHS 145C.

*Color at internodes*.—Yellow-green, nearest to RHS 145C.

*Pubescence*.—Glabrous.

Foliage:

*Arrangement*.—Distichous.

*Dimensions*.—22.4 cm long, excluding the sheath, and 2.2 cm wide.

*Shape of blade*.—Ligulate; moderately to strongly carinate.

*Aspect*.—Moderately to strongly curved.

*Apex*.—Unequal praemorse.

*Base*.—Sheathing.

*Sheath dimensions*.—4.0 cm long and 1.5 cm wide, on average.

*Sheath color*.—Yellow-green, nearest to in between RHS 145B and 150C.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Green, nearest to RHS 143A, and darker towards the apex and the margins, nearest to RHS 137A. Juvenile foliage, abaxial surface — Green, nearest to RHS 143A, and darker towards the apex and the margins, nearest to RHS 137A. Mature foliage, adaxial surface — Green, nearest to RHS NN137A but slightly darker. Mature foliage, abaxial surface — Yellow-green, nearest to RHS 147B.

*Venation*.—Parallel.

*Venation color, adaxial surface*.—Green, nearest to RHS NN137A.

*Venation color, abaxial surface*.—Yellow-green, RHS 144A.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 15.

*Flowers per plant*.—10 open flowers and 5 flower buds.

*Inflorescence height*.—Approximately 20.8 cm (measured from base of lowest flower to top of upper flower).

*Inflorescence diameter*.—Approximately 15.8 cm.

*Peduncle*.—Dimensions — Approximately 38.1 cm long and 0.7 cm wide. Aspect — Generally at a 27.5 degree angle to lateral branch axis. Strength — Moderately strong. Texture and luster — Glabrous and slightly glossy. Color — Yellow-green, nearest to RHS 144A.

Bud:

*Length*.—Average of 2.3 cm.

*Diameter*.—Average horizontal diameter is 1.9 cm; the vertical diameter is 2.0 cm.

*Shape*.—Cubic, with a deltoid apex which is pointed downward.

*Pubescence, texture and luster*.—Glabrous, smooth and matte.

*Color*.—Yellow-green, nearest to RHS 150D, and suffused with purple towards the apex, nearest to a combination of RHS N78A and N78C; flower buds are lightly dotted purple, nearest to RHS N77B.

Flower:

*Flower type*.—Zygomorphic (orchidaceous), typical shape for the genus *Vanda*.

*Flowering habit*.—Moderately free flowering.

*Shape*.—Zygomorphic; single; consisting of three sepals and three petals, one of which is transformed into a labellum; the two lateral petals moderately overlap the lateral sepals and slightly overlap the dorsal sepal; lateral sepals slightly overlap one another.

*Aspect*.—Flowers are outward-facing to slightly nodding.

*Vertical height*.—Approximately 10.2 cm.

*Diameter*.—Approximately 9.2 cm.

*Depth*.—Approximately 3.4 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.9 cm. Width — Approximately 4.4 cm. Shape — Broad obovate. Apex — Undeeply broad emarginate. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Nearest to in between purple, RHS 76D, and white, RHS N155B, and suffused with purple towards the apex, nearest to NN78D but slightly lighter; petal is heavily dotted red-purple, nearest to a combination of RHS 71A and 72B. Color when opening, lower surface — Nearest to in between purple, RHS 76D, and white, RHS N155B, and suffused with purple towards the apex, nearest to a combination of N80B and N80C. Color when fully opened, upper surface — Purple, nearest to RHS 77B, and darker towards the margins and apex, nearest to RHS N78B; fading lighter towards the base, nearest to RHS 77D; petal is heavily dotted red-purple, nearest to a combination of RHS 71A and 72B. Color when fully opened, lower surface — Purple-violet, nearest to a combination of RHS N80C and N80D, and darker towards the margins and apex, nearest to RHS N80A. Fading, upper surface — Not fading. Fading, lower surface — Not fading. Venation — Densely reticulate. Venation color, fully opened, upper surface — Purple, nearest to RHS 77B, and darker towards the margins and apex, nearest to RHS N78B; fading lighter towards the base, nearest to RHS 77D; petal is heavily dotted red-purple, nearest to a combination of RHS 71A and 72B. Venation color, fully opened, lower surface — Reticulate venation is purple-violet, nearest to RHS N80B; main vein is purple, RHS NN78C.

*Labellum*.—Shape — Three-lobed; the shape of the lateral lobes is obovate, and the aspect is involute; the shape of the central lobe is broad oblong, and the aspect is strongly revolute. Length — Central lobe — Approximately 2.2 cm. Lateral lobes — Approximately 0.9 cm. Width — Central lobe — Approximately 1.3 cm; 0.9 at the apex. Lateral lobes — Approximately 0.6 cm. Apex — Central lobe — Deep emarginate. Lateral lobes — Obtuse. Base — Central lobe — Cuneate. Lateral lobes — Cuneate. Margin — Central lobe — Entire; slightly undulated. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte with the exception of the apex which is slightly glossy. Lateral lobes — Glabrous, velvety, and matte. Color when opening, upper surface — Central lobe — Pink, nearest to RHS NN74A, and suffused with red-purple towards the apex, nearest to RHS 72A; base is suffused with red-purple, nearest to RHS 71A; margins towards the base are purple, nearest to in between RHS N78C and N78D. Lateral lobes — Nearest to in between purple, RHS 75D, and white, RHS N155A; radially striped and suffused with purple, nearest to a combination of RHS 77A and N78B. Color when opening, lower surface — Central lobe — Purple, nearest to RHS N78A, and slightly darker towards the apex, nearest to RHS N78A but darker; base is suffused with purple, nearest to in between RHS 75C and 75D. Lateral lobes — Nearest to in between purple, RHS 75D, and white, RHS N155A; radially striped and suffused with purple, nearest to RHS 77C. Color when fully opened, upper surface — Central lobe — Red-purple, nearest to RHS NN74A, and darker towards the apex, nearest to RHS 72A but slightly darker; base is dark red-purple, nearest to RHS 71A; margins towards the base are purple, nearest to in between RHS N78C and N78D. Lateral lobes —

Nearest to in between purple, RHS 75D, and white, RHS N155A; radially striped and suffused with purple, nearest to a combination of RHS 77A and N78B. Color when fully opened, lower surface — Central lobe — Purple, nearest to RHS N78A, and slightly darker towards the apex, nearest to RHS N78A but darker; base is suffused with purple, nearest to in between RHS 75C and 75D. Lateral lobes — Nearest to in between purple, RHS 75D, and white, RHS N155A; radially striped and suffused with purple, nearest to RHS 77C. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.5 cm long and 0.75 cm wide, on average. Color — Purple, nearest to RHS N78A; slightly darker at the apex, nearest to RHS N78A, and fading lighter towards the base, nearest to RHS 75C.

*Spurs*.—Quantity — Average of 1. Length — Approximately 0.7 cm. Diameter — Approximately 0.4 cm. Vertical height — Approximately 0.8 cm, at the base. Shape — Short triangular; flattened. Apex — Bluntly acute. Base — Broad cuneate. Pubescence, texture and luster — Glabrous, smooth, and matte. Color — Nearest to in between purple, RHS 75D, and white, RHS N155A; radially striped and suffused with purple, nearest to RHS 77C.

*Sepals*.—Quantity — Average of 3 unfused sepals. Arrangement — One dorsal sepal and two lateral sepals. Length — Dorsal sepal — Approximately 5.2 cm. Lateral sepals — Approximately 5.2 cm. Width — Dorsal sepal — Approximately 4.3 cm. Lateral sepals — Approximately 5.0 cm. Shape — Dorsal sepal — Broad ovate. Lateral sepals — Broad ovate. Apex — Dorsal sepal — Undeeply emarginate. Lateral sepals — Obtuse. Base — Dorsal sepal — Cuneate. Lateral sepals — Cuneate. Margin — Dorsal sepal — Entire; very slightly undulated. Lateral sepals — Entire; very slightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Nearest to in between purple, RHS 76D, and white, RHS N155B, and suffused with purple towards the apex, nearest to NN78D but slightly darker; sepal is heavily dotted red-purple, nearest to in between RHS 71A and 72B. Lateral sepals — White, nearest to in between RHS 76D and NN155D, and suffused with purple-violet towards the margins, nearest to RHS N80B; sepals are heavily dotted red-purple, nearest to RHS 71A. Color when opening, lower surface — Dorsal sepal — Nearest to in between purple, RHS 76D, and white, RHS N155B, and suffused with purple towards the apex, nearest to in between RHS N80B and N80C; veined purple, RHS N80C. Lateral sepals — Nearest to in between purple, RHS 76D, and white, RHS N155B, and suffused with purple towards the apex, nearest to in between RHS N80B and N80C; veined purple, RHS N80C. Color when fully opened, upper surface — Dorsal sepal — Purple, nearest to RHS 77B, and darker towards the margins and apex, nearest to RHS N78B; fading lighter towards the base, nearest to RHS 77D but lighter; sepal is very heavily dotted red-purple, nearest to a combination of RHS 71A and 72B. Lateral sepals — Purple, nearest to RHS 77B, and darker towards the margins and apex, nearest to in between RHS NN78B and NN78C; fading lighter towards the base, nearest to RHS 77D but lighter; sepals are very heavily dotted and blotched red-purple, nearest to a combination of RHS 71A and 72B. Color when fully opened, lower surface — Dorsal sepal — Purple, nearest to in between RHS N75C and N75D, and darker towards the apex, RHS N78B. Lateral sepals — Purple, nearest to in between RHS N75C and N75D, and darker towards the apex, RHS N78B. Fading, upper surface — Not fading. Fading, lower surface — Not fading. Venation — Densely reticulate. Venation color, fully opened, upper surface — Dorsal sepal — Purple, nearest to RHS 77B, and darker towards the margins and apex, nearest to RHS N78B; fading lighter towards the base, nearest to RHS 77D but lighter; sepal is very heavily dotted red-purple, nearest to a combination of RHS 71A and 72B. Lateral sepals — Purple, nearest to RHS 77B, and darker towards the margins and apex, nearest to in between RHS NN78B and NN78C; fading lighter towards the base, nearest to RHS 77D but lighter; sepal is very heavily dotted red-purple, nearest to a combination of RHS 71A and 72B. Venation color, fully opened, lower surface — Dorsal sepal — Purple, nearest to in between RHS N78C and N78D, and darker towards the apex, nearest to RHS N78B. Lateral sepals — Purple, nearest to in between RHS N78C and N78D, and darker towards the apex, nearest to RHS N78B.

*Pedicels*.—Length — Approximately 5.5 cm. Diameter — Approximately 0.4 cm. Angle — Approximately 70 degree angle to peduncle axis. Strength — Moderate. Texture — Glabrous, axially angled with 5 "ribs", axially twisted (due to resupination). Luster — Glossy. Color — Purple, nearest to in between RHS 75A and 75B.

*Bract*.—Quantity — One bract present at the base of each pedicel. Shape — Obovate; folded around the base of each pedicel. Dimensions — Average of 1.8 cm long and 1.3 cm wide. Apex — Broad obtuse. Base — Broad cuneate. Margins — Entire. Color, inner surface — Yellow-green, nearest to a combination of RHS 151B to 151C. Color, outer surface — Yellow-green, nearest to a combination of RHS 151B to 151C.

Reproductive organs:

*Column*.—Length — Approximately 0.6 cm. Diameter — Approximately 0.7 cm. Color — Purple, nearest to RHS 75A.

*Ovary*.—Position — Inferior. Diameter — Approximately 0.5 cm. Color — Yellow-green, nearest to RHS 150C.

*Pollinia color*.—Yellow-orange, nearest to RHS 17B.

Seed and fruit: No fruit and seed production has been detected to date.

COMPARISON WITH THE PARENT PLANTS

Plants of the new cultivar 'SPCDW1608' differ from the *Vanda* seed parent, 'M38BP' (not patented), by the characteristics described in Table 1.

TABLE 1

| Characteristic | 'SPCDW1608' | 'M38BP' |
|---|---|---|
| Plant size. | Smaller than 'M38BP'. | Larger than 'SPCDW1608'. |
| Height of the inflorescence. | Taller than 'M38BP'. | Shorter than 'PCDW1608'. |
| Flower size. | Smaller than 'M38BP'. | Larger than 'SPCDW1608'. |
| General coloration of the petals and sepals (excluding the overlaid color pattern) when fully opened. | Lighter pink. | Darker pink. |
| Color pattern on the petals and sepals. | More heavily dotted. | Less heavily dotted. |

Plants of the new cultivar 'SPCDW1608' differ from the *Vanda* pollen parent, *Vanda* 'M409' (not patented), by the characteristics described in Table 2.

TABLE 2

| Characteristic | 'SPCDW1608' | 'M409' |
|---|---|---|
| Flower size. | Larger than 'M409'. | Smaller than 'SPCDW1608'. |
| General coloration of the petals and sepals (excluding the overlaid color pattern) when fully opened. | Lighter pink. | Darker pink. |

TABLE 2-continued

| Characteristic | 'SPCDW1608' | 'M409' |
|---|---|---|
| Color pattern on the petals and dorsal sepal. | Dots on the petals and dorsal sepal are more prominent. | Dots on the petals and dorsal sepal are less prominent. |

COMPARISON WITH THE MOST SIMILAR *VANDA* CULTIVAR KNOWN TO THE INVENTOR

Plants of the new cultivar 'SPCDW1608' are most similar to the cultivar, *Vanda* 'SPCDW1510' (U.S. patent application Ser. No. 14/999,832). A comparison of 'SPCDW1608' with *Vanda* 'SPCDW1510' is described in Table 3.

TABLE 3

| Characteristic | 'SPCDW1608' | 'SPCDW1510' |
|---|---|---|
| General coloration of the petals and sepals (excluding the overlaid color pattern) when fully opened. | Light pink. | Darker pink. |
| Color pattern on the petalsm and dorsal sepal. | Heavily dotted with dark red-purple. | Moderately dotted blotched with a lighter shade of red-purple. |
| Color pattern on the lateral sepals. | Heavily dotted and blotched with dark red-purple. | Irregularly blotched and tessellated with lighter red-purple. |
| Petal and sepal margins. | Less undulated than 'SPCDW1510'. | More undulated than 'SPCDW1608'. |
| General coloration of the lateral sepals. | Darker pink. | Lighter pink. |
| Width of the central lobe of the labellum. | Wider than 'SPCDW1510'. | Narrower than 'SPCDW1608'. |
| General coloration of the column. | Light purple. | Darker purple. |

That which is claimed is:

1. A new and distinct variety of *Vanda* plant named 'SPCDW1608', substantially as described and illustrated herein.

* * * * *